(12) United States Patent
Yasumura et al.

(10) Patent No.: US 7,297,307 B2
(45) Date of Patent: Nov. 20, 2007

(54) ABSORBENT MEMBER AND A METHOD OF PRODUCING AN ABSORBENT MEMBER

(75) Inventors: Daisuke Yasumura, Tochigi (JP); Masato Oshima, Tochigi (JP)

(73) Assignee: Kao Corporation, Tokyo (JP)

( * ) Notice: Subject to any disclaimer, the term of this patent is extended or adjusted under 35 U.S.C. 154(b) by 788 days.

(21) Appl. No.: 10/456,833

(22) Filed: Jun. 9, 2003

(65) Prior Publication Data

US 2003/0236510 A1 Dec. 25, 2003

(30) Foreign Application Priority Data

| Jun. 10, 2002 | (JP) | ............................. 2002-168650 |
| Jun. 10, 2002 | (JP) | ............................. 2002-168651 |
| Apr. 16, 2003 | (JP) | ............................. 2003-112200 |
| Apr. 25, 2003 | (JP) | ............................. 2003-121073 |
| Apr. 25, 2003 | (JP) | ............................. 2003-121074 |

(51) Int. Cl.
*B27N 3/04* (2006.01)
*A61F 13/15* (2006.01)

(52) U.S. Cl. ..................... 264/517; 264/518; 425/80.1; 425/83.1

(58) Field of Classification Search ..................... None
See application file for complete search history.

(56) References Cited

U.S. PATENT DOCUMENTS

| 4,610,678 A | 9/1986 | Weisman et al. |
| 4,666,647 A | 5/1987 | Enloe et al. |
| 4,761,258 A | 8/1988 | Enloe |
| 5,370,007 A | 12/1994 | Komarek |
| 5,601,545 A | 2/1997 | Glaug et al. |
| 6,310,268 B1 | 10/2001 | Rangachari et al. |
| 6,630,088 B1 * | 10/2003 | Venturino et al. ........... 264/121 |
| 6,630,096 B2 * | 10/2003 | Venturino et al. ........... 264/518 |
| 6,848,894 B2 * | 2/2005 | Baker et al. ................ 425/81.1 |

FOREIGN PATENT DOCUMENTS

| EP | 0226939 A2 | 7/1987 |
| EP | 1210925 A2 | 6/2002 |
| JP | 59-193416 U | 12/1984 |
| JP | 61-502 A | 1/1986 |
| JP | 62-206071 A | 9/1987 |
| JP | 2-5945 A | 1/1990 |
| JP | 8-66426 A | 3/1996 |
| JP | 2000-178866 A | 6/2000 |
| JP | 2000-234255 A | 8/2000 |

* cited by examiner

*Primary Examiner*—Mary Lynn Theisen
(74) *Attorney, Agent, or Firm*—Birch, Stewart, Kolasch & Birch, LLP (57) ABSTRACT

The present invention relates to a method of producing an absorbent member comprising feeding a superabsorbent polymer and pul fiber both in the form of a dispersion in an air stream, depositing the superabsorbent polymer and the pulp fiber in a recess by suction through a plurality of suction holes provided in the bottom of the recess and releasing the deposited aggregate from the recess. The bottom of the recess (50) has a first suction region having an open area ratio R1 of 40 to 80% and a second suction region having an open area ratio R2 of 2 to 20% with the ratio of R1 to R2 ranging from 70/30 to 99/1. The superabsorbent polymer and the pulp fiber are deposited on both the first and the second suction regions.

The present invention also relates to an absorbent member comprising a superabsorbent polymer and pulp fiber.

8 Claims, 5 Drawing Sheets

ABSORBENT MEMBER AND A METHOD OF PRODUCING AN ABSORBENT MEMBER

FIELD OF THE INVENTION

The present invention relates to absorbent members containing superabsorbent polymer and pulp fiber and a method for producing an absorbent member.

BACKGROUND OF THE INVENTION

In general, the absorption capacity of an absorbent article is designed according to the intended use. Disposable diapers, for example, are used for a wide range of wearers from newborns to adults who need care and should be designed to have varied absorption capacities according to the wearer.

For instance, disposable diapers for newborns, who usually have loose and runny stools, should be designed to have enhanced stool absorbency in the portion from the longitudinal middle to the rear (back side). Some of those for infants or adults are designed to have increased stool absorption performance in the portion from the longitudinal middle to the front (stomach side) so as to absorb a large quantity of urine. The former diapers (for newborns) may hardly leak even without a high total absorption capacity. On the other hand, the latter diapers (for infants or adults), which are chiefly contemplated for absorbing a large quantity of urine, must have an increased absorption capacity in the portion from the longitudinal middle to the front. Known techniques for meeting this demand include (i) fabricating an absorbent member having a polymer-rich front portion by patternwise scattering superabsorbent polymer particles and (ii) fabricating an absorbent member having a two-ply structure in the front portion (e.g., JP-A-8-66426).

The method involving patternwise scattering superabsorbent polymer particles requires not only a special patternwise scattering unit but a unit for precisely positioning a scattering pattern on sheeting on which the polymer is scattered. Additionally, it is difficult to monitor the position of the scattering pattern on the production line. Sometimes there are cases in which the polymer particles fall off from the polymer-rich portion, or the polymer particles can cause gel blocking while in use, failing to exhibit absorption capability as expected.

An absorbent member having a two-ply structure only in the front portion thereof includes (a) one composed of a lower absorbent layer and a separately prepared upper absorbent layer laid on part of the lower absorbent layer and (b) one prepared by turning up a single-layered absorbent member to make a two-plied portion. Both absorbent members (a) and (b) require complicated equipment for production and are therefore costly for performance. That is, production of the former (a) involves fabricating two different absorbent layers and therefore needs as many apparatus (e.g., air-laying apparatus) as the absorbent layers. Production of the latter (b) requires an extract folding machine, etc. Moreover, the polymer of the upper ply can cause gel blocking upon absorption and swelling, which may hinder smooth migration of the absorbed liquid to the lower ply. It can follow that the absorbent member fails to manifest the absorbing performance in parallel to the amount of the absorbing materials, such as a polymer and pulp fiber. Gel blocking can also cause leaks. Furthermore, these absorbent members with a two-ply structure only in the front portion unavoidably have a difference in stiffness between the two-plied front portion and the single-plied rear portion, which can give a wearer discomfort.

JP-A-62-206071 discloses a technique for producing an absorbent pad having a higher basis weight in a certain zone than other zones, in which a web-forming plate on which a fibrous material is air-laid has a specifically contoured recess, and the space under the recess is designed so as to apply a high negative pressure to the recess. The publication refers only to deposition of a fibrous material, being silent on a mixed system of a superabsorbent polymer and pulp. Furthermore, because the web-forming plate has, in the zone where fibers are to be deposited with a higher basis weight, a recess surrounded by tapered walls, the suction force is not directly exerted to this zone. It is very likely that the resulting fiber-laid structure has physical discontinuity between the portion formed in the recess and the portion formed on the flat zone of the web-forming plate.

JP-A-2000-234255 discloses a method of producing an air-laid fiber article having regions which are different in height and density which comprises accumulating a raw material by suction in a recess having openings, wherein the recess has its bottom divided into a plurality of suction regions having different open area ratios. The publication has no mention of production using a mixed system of a superabsorbent polymer and pulp fiber. There is a description about the technique for providing the bottom of the recess with a level difference so as to control the height and density, but there is no description about controlling the basis weight. Besides, there is a possibility that the absorbent member thus produced becomes out of shape because of this level difference while the absorbent member is conveyed.

Absorbent members comprising a cellulosic fiber, such as pulp fiber, and a polyacrylic acid-based absorbent polymer have been widely used in absorbent articles for absorbing and retaining liquid body waste, such as disposable diapers, sanitary napkins, and panty liners. Absorbent members of the same composition have come to be employed for other applications.

In the development and quality evaluation of these kinds of products, it is beneficial to accurately determine the amount of the fiber and/or the absorbent polymer making up the absorbent member. However, conventional methods of quantitative determination have such disadvantages as low accuracy and a complicated operation.

It is possible, for example, that an absorbent member made of an absorbent polymer and pulp fiber is disintegrated and separated by screening through a sieve of prescribed mesh size into the absorbent polymer and the pulp fiber. However, it is difficult to choose a sieve of proper mesh size unless the particle size of the absorbent polymer and the fiber length of the pulp fiber are known. Even though a proper sieve is selected, time-consuming and laborious procedures, such as condition setting, have to be taken so as to minimize scatter of measured values, and measurement must be repeated for accuracy.

SUMMARY OF THE INVENTION

The present invention provides in its first aspect a method of producing an absorbent member comprising feeding a superabsorbent polymer and pulp fiber both in the form of a dispersion in an air stream, depositing the superabsorbent polymer and the pulp fiber in a recess by suction through a plurality of suction holes provided in the bottom of the recess, and releasing the deposited aggregate from the recess, wherein the bottom of the recess has a first suction region having an open area ratio R1 of 40 to 80% and a second suction region having an open area ratio R2 of 2 to 20% with the ratio of R1 to R2 ranging from 70/30 to 99/1, and the superabsorbent polymer and the pulp fiber are deposited on both the first and the second suction regions.

The present invention provides in its second aspect an absorbent member comprising a superabsorbent polymer and pulp fiber which has a high basis weight portion having a high content of the superabsorbent polymer per unit area and a high content of the pulp fiber per unit area and a low basis weight portion having a lower content of the superabsorbent polymer per unit area and a lower content of the pulp fiber each per unit area than the high basis weight portion, the high basis weight portion and the low basis weight portion being integrally formed with physical continuity.

The present invention provides in its third aspect an absorbent article comprising a liquid permeable topsheet, a liquid impermeable backsheet, and a liquid retentive absorbent member interposed between the topsheet and the backsheet and having a substantially oblong shape with longitudinal ends, wherein the absorbent member comprises a superabsorbent polymer and pulp fiber and has a high basis weight portion having a higher content of the superabsorbent polymer and a higher content of the pulp fiber each per unit area than any other portion, the high basis weight portion being disposed in an area near to one of the longitudinal ends of the absorbent article, and the high basis weight portion and the other portion being integrally formed with physical continuity.

The present invention provides in its fourth aspect a method of quantitatively determining at least one of fiber and an absorbent polymer which comprises the steps of degrading a polyacrylic acid-based absorbent polymer of a sample of a known weight comprising a cellulosic fiber and the polyacrylic acid-based absorbent polymer, removing the resulting low-molecular weight components, and measuring the weight of the residue to obtain at least one of the content of the fiber and the content of the absorbent polymer of the sample.

BRIEF DESCRIPTION OF THE DRAWINGS

The present invention will be more particularly described with reference to the accompanying drawings, in which:

FIG. 2(a) and FIG. 2(b) show the absorbent member of FIG. 1, in which

FIG. 4(a) and FIG. 4(b) illustrate an example of the configuration of a recess for fiber deposition, a first suction region, and a second suction region, in which

DETAILED DESCRIPTION OF THE INVENTION

The present invention relates to an efficient and economical method for producing an absorbent member having excellent absorbing performance (absorbency) which is designed to have an increased absorption capacity in a part and to allow that part to fully exhibit its absorbency.

The present invention also relates to an absorbent member and an absorbent article containing the same, the absorbent member being designed to have an increased absorption capacity in a part and to allow that part to fully exhibit its absorbency and, when used in an absorbent article, giving little uncomfortable feeling to a wearer.

The present invention also relates to a method of accurately determining the content of fiber and/or the content of an absorbent polymer in a mixture comprising cellulosic fiber and a polyacrylic acid-based absorbent polymer.

Figure 1:
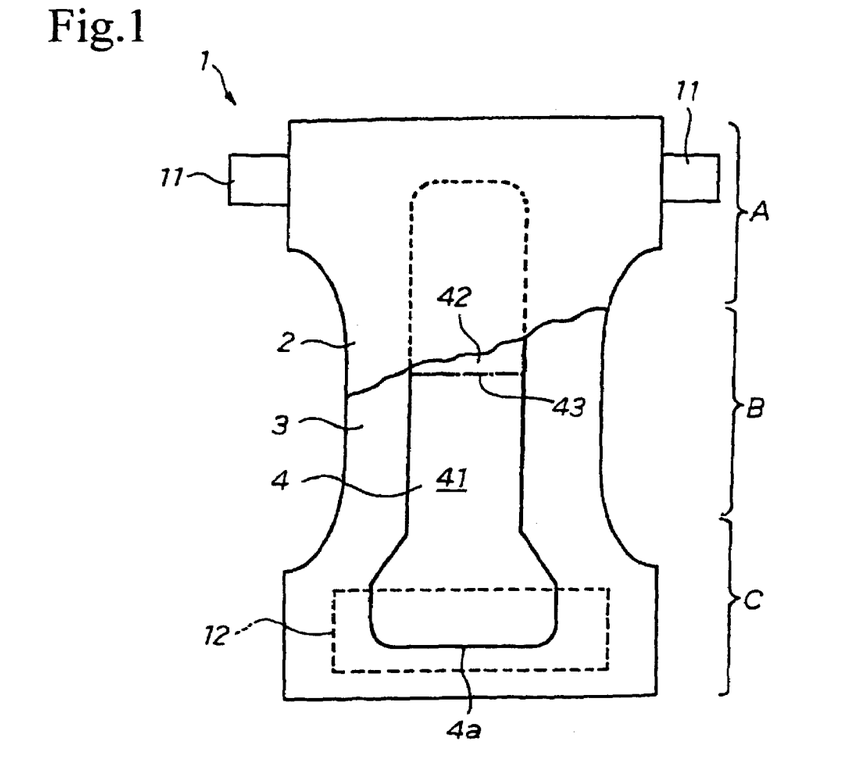
FIG. 1 is a plan view of a preferred example of an absorbent member according to the present invention in application to a disposable diaper, seen from the topsheet side with a part cut away.
Figures 2A, 2B:
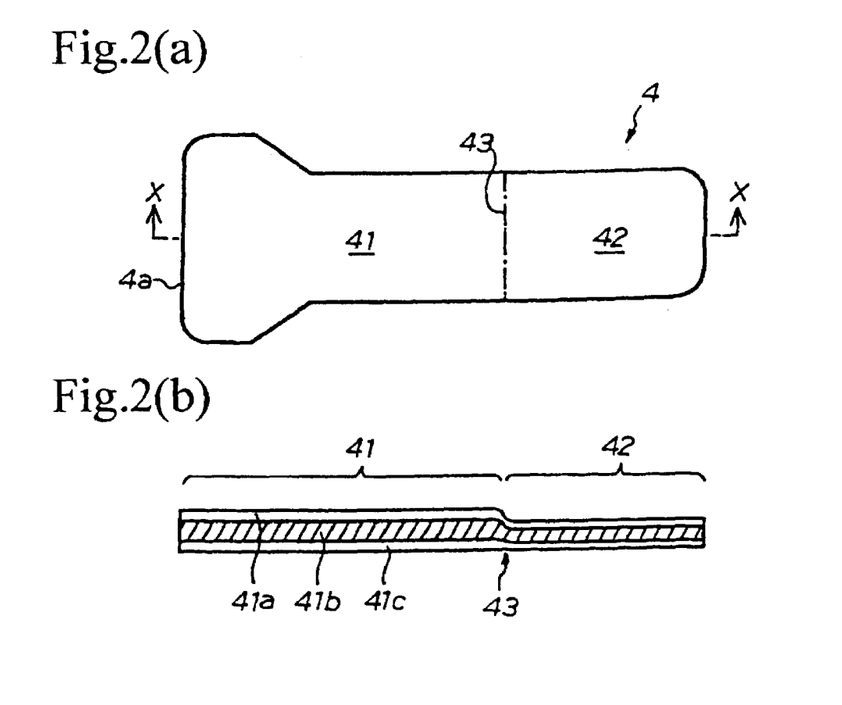
FIG. 2(a) is a plan view.
FIG. 2(b) is a schematic cross-sectional view taken along line X—X in FIG. 2(a)

A preferred embodiment of an absorbent member according to the present invention is illustrated in FIG. 1, FIGS. 2(a) and 2(b). The absorbent member 4 shown in FIG. 1, FIGS. 2(a) and 2(b) is a preferred example of an absorbent member according to the second aspect of the invention which is produced by the method according to the first aspect of the invention. FIG. 1 represents application of the absorbent member 4 as a constituent member of a disposable diaper 1 as an embodiment of an absorbent article according to the third embodiment of the invention.

The absorbent member 4 shown in FIGS. 2(a) and 2(b) is the one used in the disposable diaper 1 shown in FIG. 1. The disposable diaper 1 includes a liquid permeable topsheet 2, a liquid impermeable backsheet 3, and a liquid retentive absorbent member 4 interposed between the topsheet 2 and the backsheet 3. The disposable diaper 1 has a substantially oblong shape. The disposable diaper 1 is divided into three sections, a rear section A adapted to be applied to the back side of a wearer, a crotch section B adapted to be applied to the crotch of the wearer, and a front section C adapted to be applied to the stomach side of the wearer. It is a disposable diaper of what we call unfolded or flat type. A fastening tape 11 is provided on each side edge of the rear section A, and a landing tape 12 for receiving the fastening tapes 11 is provided on the backsheet side of the front section C.

The absorbent member 4 contains a superabsorbent polymer and pulp fiber. It may be made solely of the superabsorbent polymer and pulp fiber or may contain other components than the superabsorbent polymer and the pulp fiber. The absorbent member 4 has a high basis weight portion 41 and a low basis weight portion 42. The high basis weight portion 41 contains more superabsorbent polymer and more pulp fiber per unit area than the low basis weight portion 42.

The high basis weight portion 41 is arranged nearer to the end 4a of the absorbent member 4 which is positioned in the front section C applied to the stomach of a wearer. More specifically, the high basis weight portion 41 is arranged in the target zone of the diaper 1 facing the wearer's urethra, i.e., the area from the crotch section B to the front section C.

The high basis weight portion 41 and the low basis weight portion 42 are integrally formed with physical continuity. In other words, the two portions make a unitary structure with no interface therebetween that might be observed where separate two absorbent members are joined together. The high basis weight portion 41 is slightly thicker than the low basis weight portion 42.

The longitudinal cross-section of the absorbent member 4, including both portions 41 and 42, is different from that of a conventional absorbent member which is prepared by superimposing separately fabricated upper and lower absorbent members or turning up one end of a single-plied absorbent member. As is shown in FIG. 2(b), the absorbent member 4 is a unitary structure with no discontinuity between the high basis weight portion and the low basis weight portion.

As illustrated in FIG. 2(b), the high basis weight portion 41 and the low basis weight portion 42 each consist of three layers arranged in the thickness direction; an upper layer 41a mainly comprising pulp fiber, an intermediate layer 41b mainly comprising a superabsorbent polymer, and a lower layer 41c mainly comprising pulp fiber. Each of the layers 41a, 41b, and 41c is a physically continuous layer extending over the two portions.

A great difference between the absorbent member 4 of the present invention and a conventional one lies in that the former has no physically discontinuous region between the high basis weight portion and the low basis weight portion whereas the latter does.

The absorbent member 4 shows a basis weight difference between the high basis weight portion 41 and the low basis weight portion 42. More concretely, the basis weight steeply changes between the high basis weight portion 41 and the low basis weight portion 42 when viewed from above. This is because the deposited amounts of the pulp fiber and the superabsorbent polymer are larger in the high basis weight portion 41 than in the low basis weight portion 42 while the two portions are substantially equal in density. To achieve such a structure, technical manipulations for production that will be described infra are important.

The basis weight difference between the two portions 41 and 42 is preferably 20 to 600 g/m$^2$, particularly 30 to 200 g/m$^2$. Within this range of basis weight difference, the resultant difference in stiffness is not so large as to give discomfort to a wearer but is moderate to give a comfortable fit when worn.

The basis weight of each portion is measured as follows.

Measurement of Basis Weight:

Piece(s) of an area of at least 3 cm by 3 cm (preferably at least 5 cm by 5 cm) are cut out of each portion. The area and the weight of every piece are measured to calculate a basis weight (weight/area). Five pieces are cut out of the two portions, preferably, five pieces out of each portion.

The basis weight difference between the two portions is measured by the calculation from an average basis weight of the pieces cut out of the high basis weight portion and an average basis weight of the pieces cut out of the low basis weight portion.

The basis weight of the two portions can appropriately be decided depending on the use of the absorbent member without specific limitation. As one example, the basis weight of the high basis weight portion may be 200 to 400 g/m$^2$, and the basis weight of the low basis weight portion may be 100 to 300 g/m$^2$.

It is desirable that the mixing ratio of the superabsorbent polymer and pulp fiber be substantially equal between the high basis weight portion and the low basis weight portion. Then there will only be a little difference in the rate of absorption between the two regions, and the gel blocking problem will most likely hardly occur in the high basis weight portion. More specifically, the differences between the two portions in proportion (weight %) of the superabsorbent polymer and proportion (weight %) of the pulp fiber based on the total weight of the superabsorbent polymer and the pulp fiber in the high basis weight or low basis weight portion are each preferably within ±5%. Where, for example, the superabsorbent polymer to pulp fiber mixing ratio in the high basis weight portion 41 is 54:46, the proportion of the superabsorbent polymer in this portion is 54%, while that of the pulp fiber is 46%. In this case, where the proportion of the superabsorbent polymer in the low basis weight portion 42 is 55%, the difference in polymer proportion between the two portions is 54%–55%=–1%.

The high and the low basis weight portions of the absorbent member 4 according to the present embodiment have a substantially equal density. More specifically the ratio of the density of the high basis weight portion to that of the low basis weight portion ranges from 0.9 to 1.1. Within this density ratio range, it is easy to design the absorbing performance of the two portions and such a moderate stiffness difference between the two portions does not give discomfort. The density of each portion can be measured as follows.

Measurement of Density:

Where the high and the low basis weight portions both have a sufficient area, each portion, cut apart, is measured for volume and weight to calculate the density. Where one of the two portions is not large enough, for instance, where a plurality of high basis weight portions as small as less than 1 cm$^2$ each are distributed in the low basis weight portion, five pieces of an area of at least 3 cm by 3 cm (preferably at least 5 cm by 5 cm) are cut out of arbitrarily chosen parts of the absorbent member, provided that at least one cut piece should contain high basis weight portion, and at least one cut piece should contain low basis weight portion. Every piece is measured for volume and weight to calculate the density (weight/volume). Only if the difference in density among the five pieces is within ±5%, the high and the low basis weight portions can be seen as substantially equal in density.

In order for the high and the low basis weight portions to have substantially the same density, the method of the present invention hereinafter described may be adopted to produce the absorbent member. In this method, the two portions are controlled to have substantially the same mixing ratio of the superabsorbent polymer and the pulp fiber. No compression is given to the two portions, or the two portions are subjected to a compression treatment such that the pressure applied to the two portions is substantially equal. Such a compression treatment can be done by, for example, pressing with a plate having a level difference in conformity with the thickness difference between the two portions. The absorbent member 4 shown in FIGS. 2(a) and 2(b) has an almost equal density over the entire area.

The mixing ratio of the superabsorbent polymer in each portion 41 or 42 can be determined as follows.

Method of Measuring Polymer/Pulp Fiber Mixing Ratio:

Five pieces are cut out of an absorbent member in such a manner that at least one cut piece is cut out of the high basis weight portion and at least one cut piece is cut out of the low basis weight portion. Each cut piece is separated into the polymer or the pulp fiber by screening or like techniques. Each of the thus separated polymer and fiber is weighed. The mixing ratio is obtained as the average of each portion. Various means enabling substantially the complete separation of the polymer and the fiber can be utilized. For example, they can be separated by screening through a fine sieve making use of the difference in particle size, and the oversize particles and the undersize particles are weighed. They can also be separated by blowing air into the mixture to scatter only the pulp fiber, by making use of the difference in weight, and the weight of the mixture before being blown and that of the residue are measured.

Where polyacrylic acid-based absorbent polymers are employed, a particularly preferred method of measuring the polymer/pulp fiber mixing ratio in a sample comprising pulp fiber and an absorbent polymer comprises degrading the polymer, removing the resulting low molecular weight components of the polymer, weighing the residue, and calculating the contents of the fiber and the absorbent polymer in the sample. More concretely, a sample cut out of each of the high basis weight portion 41 and the low basis weight portion 42 is analyzed in the same manner as described in Examples of the fourth aspect of the present invention which will be given later, in which samples containing pulp fiber and absorbent polymers were analyzed. Prior to analysis, every sample is dried at 90° C. for at least 8 hours, equilibrated at room temperature, and weighed accurately.

The absorbent member 4 having the above-mentioned configuration is designed to have the high basis weight portion 41 in the area demanding a high absorption capacity and the low basis weight portion 42 in the area having a less demand for absorption capacity. By this design, absorbing materials such as a superabsorbent polymer and pulp fiber can be used most effectively, and their absorption capacities can be manifested to the full. Besides, since the high basis weight portion 41 contemplated for high absorbing performance has a single-ply structure which is not made by superposing two absorbent members, that is, its basic structure is the same as the absorbent member structure of the low basis weight portion and is not overlaid with another absorbent member, the absorbency of this portion can be manifested efficiently. That is, in a conventional two-ply absorbent member in which another absorbent member structure is overlaid on the absorbent member structure of the low absorbing performance area, cases are sometimes found in which the superabsorbent polymer in the upper ply is considerably swollen with excreta and hinders smooth passage of the excreta to the lower ply (gel blocking). Having a single ply structure, the high basis weight portion 41 allows excreta to spread throughout the whole thickness, and the polymer present in the lower part can be used effectively.

Since the high basis weight portion 41 and the low basis weight portion (other portion) have an integral structure with physical continuity, the difference in stiffness between the two portions is not so large unlike the case with the conventional two-plied absorbent member. Therefore, in application to absorbent articles such as a disposable diaper, the absorbent member 4 hardly causes discomfort to the wearer.

Furthermore, the high basis weight portion 41 and the low basis weight portion 42 are substantially equal in superabsorbent polymer/pulp fiber mixing ratio. This not only makes it possible to achieve density uniformity but facilitates designing the absorbing performance of the absorbent member. Even with the two portions being equal in density, if they are different in superabsorbent polymer/pulp fiber mixing ratio, it can happen that some part of the absorbent member has an unfavorable absorption rate or absorption capacity, and as a result, there are fears that several unfavorable problems such as leakage and polymer leakage may occur.

The disposable diaper 1, an embodiment of the absorbent article according to the third aspect of the invention, uses the above-described absorbent member 4 with the high basis weight portion 41 disposed in the target zone facing the urethra of a wearer, i.e., the zone from the stomach section C to the crotch section B. As a result, the above-mentioned advantages of the absorbent member are effectively taken of That is, the absorption capacity is effectively taken advantage of in the target zone, and even when a wearer has an unexpected excretion on the back side portion of the diaper (e.g., a watery excretion containing some solid, such as watery stool), the absorbent member of that portion is hardly clogged by virtue of the low density and efficiently makes the excrement spread toward the stomach portion.

The absorbent member 4 according to the present embodiment can be preferably produced by a combination of at least three out of the following steps or conditions (1) to (4), the combination including at least the step (1) and the condition (2).

(1) A superabsorbent polymer and pulp fiber both dispersed in an air stream are deposited in a recess formed on the peripheral surface of a forming drum by maintaining the pressure of a chamber inside the forming drum lower than atmospheric pressure by 1 to 20 kPa (preferably 5 to 20 kPa). The recited range of negative pressure makes a difference in the rate of deposition based on the difference in the open area ratio described in (2) below.

(2) The bottom of the recess has a large number of suction holes and is divided into regions different in open area ratio (ratio of the total open area of the respective regions to the area of the respective regions). The open area ratio of the region forming a high basis weight portion is 40 to 80%, and that of the region forming a low basis weight portion is 2 to 20%.

(3) The ratio of the open area ratio of the region forming a high basis weight portion to that of the region forming a low basis weight portion is from 70/30 to 99/1, preferably from 95/5 to 75/25.

(4) The bottom of the recess is as flat as possible with preferably no level difference. If there is a level difference, the air stream generated by suction would be disturbed against it, which can result in formation of an absorbent member having a physically discontinuous structure or a non-uniform density.

Figure 3:
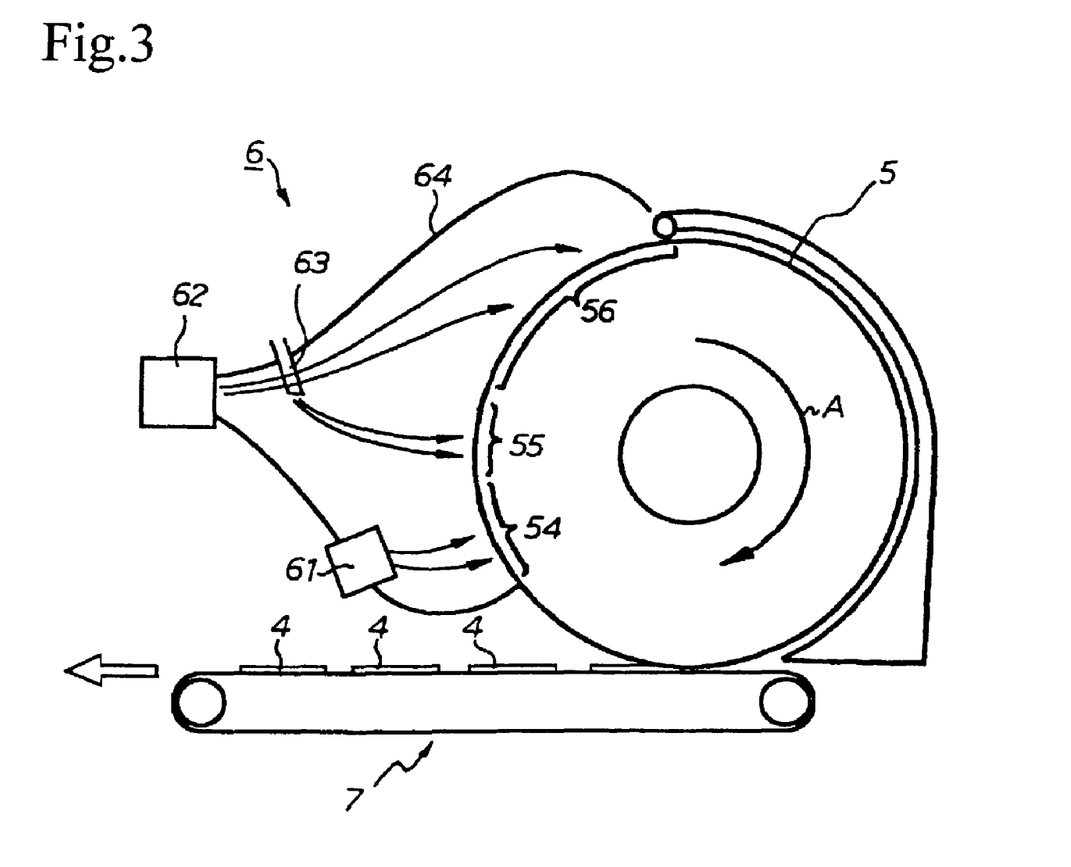
FIG. 3 schematically shows an apparatus that is preferably used to produce an absorbent member according to the present invention.

A preferred embodiment of the method of producing an absorbent member according to the present invention will be described. FIG. 3 shows an apparatus which can be preferably used to carry out the method of the invention. The apparatus shown in FIG. 3 is designed to produce the absorbent member 4 having the above-described structure.

The apparatus shown in FIG. 3 comprises a rotatable drum (forming drum) 5 having on its peripheral surface a plurality of recesses 50 the bottom of which has a large number of suction holes and a material feed system 6 for scattering and feeding raw materials of the absorbent member to the peripheral surface of the forming drum 5. The apparatus deposits the raw materials in each of the recesses by suction and successively releases the resulting air-laid aggregates from the recesses to produce the absorbent members 4 in a continuous manner.

The recesses 50 are formed on the peripheral surface of the rotatable drum 5 at a prescribed interval. The drum's outer rim having the recesses 50 rotates in the direction indicated by arrow A in FIG. 3. The inside of the rotatable drum 5 is sectioned into chambers designed to have independently controlled pressures. The chambers at the back of each area 54, 55, and 56 where the raw materials are deposited is maintained under negative pressure, and another chamber at the back of a part of the drum is kept under positive pressure. The air-laid aggregates are released from the respective recesses 50 when they come to the part where positive pressure is applied. In case where the same negative pressure is applied to the back of each area 54, 55, and 56, a common chamber located at the back of each area 54, 55, and 56 can be provided.

The material feed system 6 is configured to feed raw materials for making the absorbent member 4, i.e., a superabsorbent polymer and pulp fiber to the peripheral surface of the rotatable drum 50 in the form of a dispersion in an air stream. In detail, the system 6 includes a first and a second pulp fiber feeder 61 and 62 for feeding pulp fiber and a polymer feeder 63 for feeding a superabsorbent polymer. The first and the second pulp fiber feeders 61 and 62 each fiberize pulp sheeting into loose pulp fibers by a known mechanism and feeds the pulp fibers to the peripheral surface of the rotatable drum 5 as air-entrained fibers in an air stream generated in a duct 64 by suction. The polymer feeder 63 introduces a superabsorbent polymer into the air stream thereby feeding the polymer to the peripheral surface of the rotatable drum 5.

The superabsorbent polymer and the pulp fibers fed from the material feeding system 6 are deposited in the recesses 50 by the action of negative pressure from the rotatable drum 5 to form discrete air-laid aggregates. The aggregates are carried on the drum to a prescribed region, where they are successively released from the recesses 50 onto a conveyer belt 7.

Figure 4A:
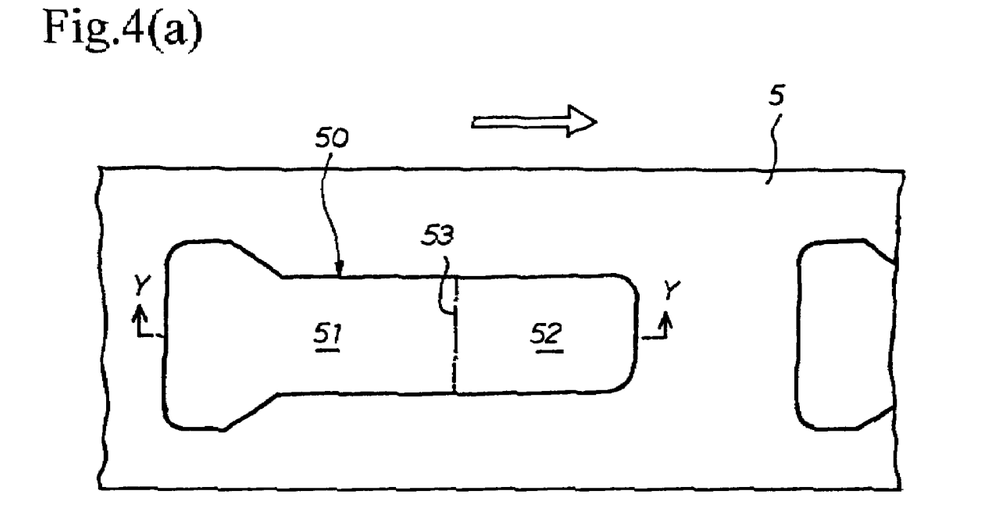
FIG. 4(a) is a partial plan view.
Figure 4B:
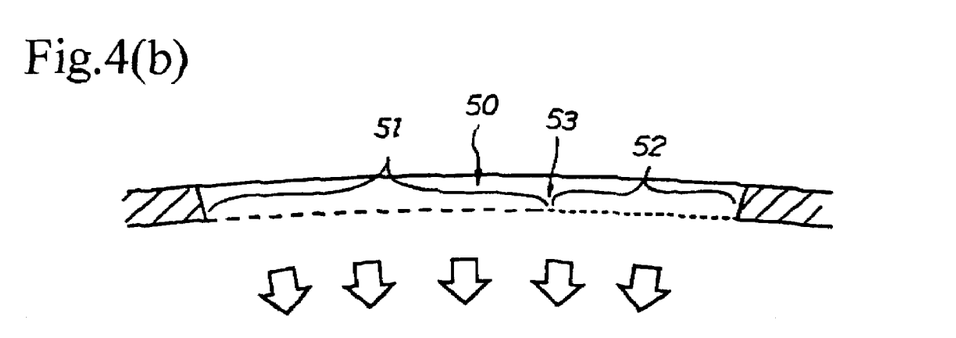
FIG. 4(b) is a schematic cross-sectional view taken along line Y—Y of FIG. 4(a)

The bottom of each recess 50 has a first suction region 51 having a high open area ratio and a second suction region 52 whose open area ratio is smaller than that of the first suction region as shown in FIGS. 4(a) and 4(b). The first suction region 51 and the second suction region 52 correspond to the high basis weight portion 41 and the low basis weight portion 42 of the absorbent member 4.

In the present invention it is not necessary to make a level difference between the first and second suction regions 51 and 52 as means for thickness control. The language "a level difference as means for thickness control" as referred to herein means a level difference for forming a thick portion and a thin portion in an absorbent member. Accordingly, such surface unevenness that would not influence the thickness of an absorbent member is not referred to as a level difference as means for thickness control.

In the method of producing an absorbent member according to the first aspect of the invention, the ratio of the open area ratio R1 of the first suction region 51 to the open area ratio R2 of the second suction region 52, namely R1/R2, ranges from 70/30 to 99/1. If the R1/R2 is less than 70/30, the difference in open area ratio is too small to form distinguishable high and low basis weight portions, that is, to produce a distinct difference in basis weight between the two portions. Where the R1/R2 is in a certain range less than 70/30 except near 50/50, the pulp/polymer mixing ratio cannot be made uniform. If the R1/R2 is more than 99/1, on the other hand, the open area ratio R2 of the second suction region 52 is too small to make the pulp/polymer mixture sufficiently deposit in the second suction region 52. In particular, the heavier polymer is liable to be concentrated at the first suction region, resulting in the extremely uneven distribution of the pulp fiber and the absorbent polymer.

In order to ensure the probability of equalizing the pulp/polymer mixing ratio over the entire area, it is particularly preferred that the R1/R2 be in a range of from 75/25 to 95/5.

In the method of the present invention, the open area ratio R1 of the first suction region 51 is 40 to 80%, and the open area ratio R2 of the second suction region 52 is 2 to 20%. If R1 is less than 40%, a sufficient air flow is not generated. It follows that the polymer is stalled and is not sufficiently mixed into the pulp fiber. If R1 is more than 80%, excessive air flow may cause the pulp/polymer mixture to clog the suction holes of the recesses.

If R2 is less than 2%, air-laying stability will be impaired, tending to result in shape deficiency or folding or turnup of the absorbent member. If R2 exceeds 20%, the low basis weight portion is hard to form. If R2 exceeds 30%, the low basis weight portion is not formed.

In order to produce an absorbent member excellent in uniformity of the pulp/polymer mixing ratio and shape retention, R1 is preferably 45 to 58%. In order to obtain uniformity of the pulp/polymer mixing ratio and to facilitate realization of uniformity in pulp/polymer mixing ratio even with an increased polymer proportion, R2 is preferably 3 to 18%.

The open area ratio R, inclusive of R1 and R2, is calculated from equation (1):

$$R = (S2/S1) \times 100 \tag{1}$$

wherein S1 is the area of each suction region, inclusive of the total area of suction holes; and S2 is the total area of suction holes in each suction region.

A difference in open area ratio R between the first and the second suction regions 51 and 52 can be made by (i) forming suction holes of a size (e.g., diameter) at pitches different between the two regions, (ii) forming suction holes of different sizes (e.g., diameter) between the two regions at the same pitch, (iii) forming suction holes of different sizes at different pitches between the two regions, or like methods. The method (i) is adopted in Examples given later.

It is preferred that the suction holes preferably have an average diameter of 0.05 to 0.5 mm in both regions 51 and 52 and that the diameter of substantially all the suction holes fall within this range. The suction holes are preferably truly circular. Where they are elliptic, a circle-equivalent diameter is taken as the diameter of the holes.

In the apparatus shown, the bottom of the recesses is formed of a metal sheet having a large number of circular through-holes made by punching, namely, punching metal, the holes of which are arranged such that the lines connecting the centers of neighboring holes make a triangle.

The method of producing an absorbent member by use of the apparatus is carried out as follows. The rotatable drum 5 is rotated in the direction indicated by arrow A at a constant speed. The chambers in the rotatable drum 5 which are located at the back of areas 54, 55, and 56 where the raw materials are to be deposited in the recess 50 are evacuated to exert a suction force to the suction holes. The application of negative pressure to these areas creates an air stream in the duct 64 which entraps the raw materials.

The raw materials introduced into the duct 64 are entrapped and dispersed in the air stream in a mixed state, carried toward the rotatable drum 5, and accumulated in the recess 50 by the suction force. The expression "(entrapped and) dispersed in the air stream in a mixed state" as used above means that at least part of the superabsorbent polymer and at least part of the pulp fiber are mixed up in a state dispersed in an air stream. In the present embodiment, the pulp and the polymer fed from the respective feed ports are dispersed in an air stream and carried to the recess and accumulated there with at least part of the pulp and at least part of the polymer being mixed up.

In depositing the superabsorbent polymer and the pulp fiber in the recess 50 by suction, it is preferred that vacuum pressure, that is lower than atmospheric pressure by 1 to 20 kPa, particularly 5 to 20 kPa, still particularly 5 to 15 kPa, be applied to the first and the second suction regions 51 and 52 from behind the bottom of the recess 50. This range of vacuum pressure is preferred for creating different basis weights between the two regions (for unevenly distributing the pulp/polymer mixture) without forming a boundary of physical discontinuity between the two regions while maintaining the pulp/polymer mixing ratio almost constant.

Vacuum pressure of the above-recited range can be applied to the first and second suction regions 51 and 52 of each recess by evacuating (a) the chamber behind the area 54 where the pulp fiber from the first pulp fiber feeder 61 is accumulated, (b) the chamber behind the area 55 where the superabsorbent polymer is accumulated or (c) the chamber behind the area 56 where the pulp fiber from the second pulp fiber feeder 62 is accumulated to create a vacuum in the above-recited range in the chamber. It is preferred that the vacuum pressure of all the chambers behind the areas 54 to 56 where the superabsorbent polymer and/or the pulp fiber are accumulated be in the above-recited range. The method in which at least the chamber at the back of the area 54 where the pulp fiber from the first pulp fiber feeder 61 is to be accumulated is evacuated to the negative pressure within the above range is preferred because the pressure applied can be measured accurately before the raw material is deposited in the recess 50.

In this embodiment, the raw materials are deposited in each recess 50 substantially in the order of the pulp fiber, the superabsorbent polymer, and the pulp fiber. Meanwhile the air-laid aggregate is given a certain shape. The air-laid aggregates are released from the respective recesses in succession at the lowest part of the rotating drum 5. The rotatable drum 5 continues rotating to repeatedly carry out suction air-laying of the raw materials and release of the air-laid aggregates to produce the absorbent members 4 efficiently and continuously.

According to the above-described method, an absorbent member having high absorbency which is designed to have an increased absorption capacity in one part and to allow that part to fully exhibit its absorbency can thus be produced efficiently and economically by means of simple equipment.

The materials forming the absorbent member 4 and the disposable diaper 1 according to the present invention are described.

The superabsorbent polymer includes various known types, such as sodium polyacrylate, acrylic acid-vinyl alcohol copolymers, crosslinked sodium polyacrylate, starch-acrylic acid graft copolymers, isobutylene-maleic anhydride copolymers and saponification products thereof, and polyaspartic acid. The raw materials of the absorbent member include not only the superabsorbent polymer and pulp fiber but hydrophilic fibers, such as rayon, cotton, and cellulose acetate, polyolefin fibers, such as polyethylene and polypropylene, condensed polymer fibers, such as polyester and polyamide, and fibers of vinyl polymers, such as polyvinyl chloride resins and polyvinyl acetate resins. The absorbent member may be covered with a sheet, such as paper or liquid permeable nonwoven fabric.

Where other fibers are added to the pulp fiber to be used as a material of the absorbent member, the differences in weight proportion (weight %) of the total amount of fiber and the amount of superabsorbent polymer respectively, between the high basis weight portion and low basis weight portion of the absorbent member, is preferably within ±5%. The weight % is based on the total weight of the superabsorbent polymer and total amount of fibers in the high basis weight portion or low basis weight portion, as applicable.

The total proportion of the absorbent polymer and the pulp fibers in the absorbent member is preferably 70 to 100%, particularly 80 to 100%.

The topsheet 2, the backsheet 3, the fastening tapes 11, and the landing tape 12 can be of any materials that have been used in conventional disposable diapers or like absorbent articles.

Figure 6A:
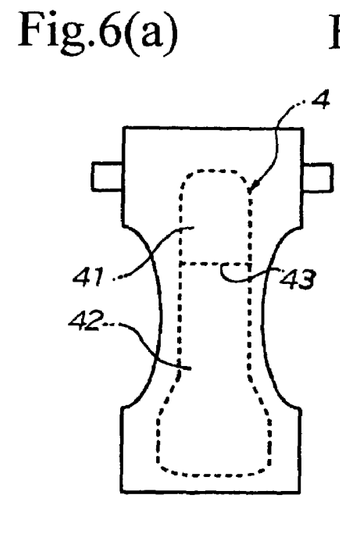
FIG. 6(a), FIG. 6(b), and FIG. 6(c) show other examples of the absorbent member and a preferred embodiment of an absorbent article according to the present invention.
Figure 6B:
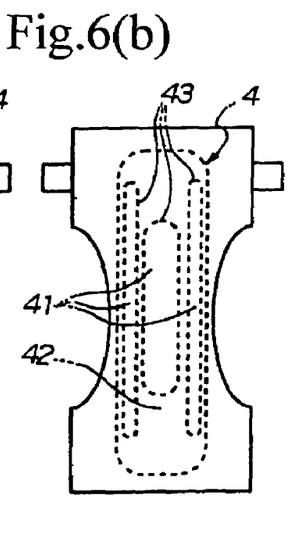
Figure 6C:
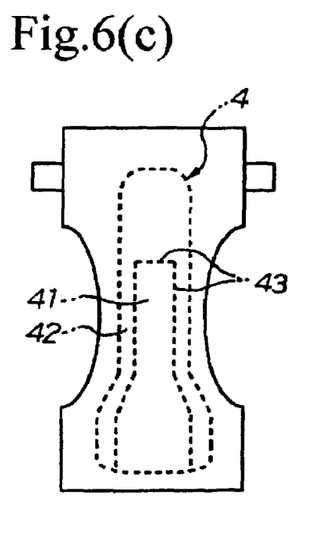

The first to third aspects of the present invention are not limited to the aforesaid embodiments. For example, the high basis weight portion 41 of the absorbent member 4 can be formed in the pattern depicted in FIGS. 6(*a*), 6(*b*) or 6(*c*), in which numeral 43 indicates the boundary between the high basis weight portion 41 and the other portion, namely the low basis weight portion 42, across which the basis weight differs.

The absorbent member 4 shown in FIG. 6(*a*) has a high basis weight portion 41 located in the area that is to be disposed in the rear section of a disposable diaper. The absorbent member 4 of FIG. 6(*a*) is specially suited to application to disposable diapers for newborns. A disposable diaper using this absorbent member 4 is effective to prevent watery stools from migrating to the stomach side to soil the wearer's front.

The absorbent member 4 shown in FIG. 6(*b*) has a high basis weight portion 41 on the widthwise middle and both sides thereof. A disposable diaper using this absorbent member is effective at preventing side leakage that may occur when a wearer, especially an aged wearer, is lying on his or her side.

While the absorbent member of the present invention has been described with particular reference to application to unfolded flat type of disposable diapers for babies, infants, and adults, the absorbent member of the present invention is applicable to so-called pull-up diapers, sanitary napkins, incontinence pads, and panty liners as well. The absorbent member of the present invention is also applicable to drip absorbing pads, absorbing sheets for kitchen use, cleaning sheets for housekeeping, pet toilet sheets, and so forth.

The apparatus for producing the absorbent member may have a single pulp fiber feeder in place of the two pulp fiber feeders. In this case, the pulp fiber is fed from one feeder into the duct.

The fourth aspect of the present invention will then be described. The cellulosic fiber which can be determined by the determining method of the invention includes pulp fiber and chemically modified pulp. The determining method is particularly suited to quantitatively determining pulp fiber.

The absorbent polymer which can be determined by the method of the invention includes various polyacrylic acid-based absorbent polymers commonly employed in absorbent articles such as disposable diapers, sanitary napkins, and panty liners. Examples of such polyacrylic acid-based polymers are polymers of acrylic acid or an alkali metal acrylate, an acrylic acid-vinyl alcohol copolymer, crosslinked sodium polyacrylate, a starch-acrylic acid graft copolymer, and an acrylic acid salt graft copolymer.

The determining method comprises the step of degrading the absorbent polymer of a sample into low-molecular weight components thereby facilitating separation between the polymer and the fiber. The term "degrading" as used herein means reduction of molecular weight to such a degree that the gel strength of the polymer reduces sufficiently and does not always mean complete degradation into monomeric species. Accordingly, the resulting low-molecular weight components may contain not only the monomer but the dimer, the trimer, and other oligomers whose gel strength is sufficiently lowered than that of the absorbent polymer. It is desirable for easy separation from the fibrous component that the absorbent polymer be degraded to such a degree that the resulting low-molecular weight components are dispersible in water; more desirably soluble in water.

From the viewpoint of achievable degradation rate and operational simplicity, degradation of the absorbent polymer is preferably effected by ultraviolet (UV) irradiation using either a UV lamp or sunlight. The UV irradiation time depends on the amount of the sample, the UV intensity, and whether any other degradation treatment is conducted in combination. It is, for example, several hours to about one week.

Before UV irradiation, it is advisable for assuring high efficiency of irradiation that the sample be immersed in water or an aqueous solution to swell the polymer component. The soaked wet sample taken out of water or the aqueous solution is then irradiated with UV light.

To accelerate degradation, UV irradiation is preferably performed in the presence of an oxidizing agent, especially ascorbic acid. This can be done by, for example, using an aqueous solution containing 0.1 wt % or more of ascorbic acid, in which the sample is immersed.

It is advantageous and preferable to carry out UV irradiation in the presence of riboflavin because, for one thing, the progress of degradation can be confirmed by observing the disappearance of the color of the polymer colored with riboflavin and, in addition, riboflavin accelerates a photo-excited reaction, thereby to promote degradation of the polymer. This can be done by, for example, using a 0.001 to 0.02 wt % aqueous solution of riboflavin, in which the sample is immersed.

Another preferred method of degrading the absorbent polymer comprises immersing a sample comprising the fiber and the absorbent polymer in an aqueous solution containing a substance capable of cleaving the polymer chain into low-molecular weight components for a predetermined period of time. Such substances capable of cleaving the polymer chain include general oxidizing agents. It is particularly preferred to use an aqueous solution containing ascorbic acid and riboflavin.

Where UV irradiation is adopted with or without an oxidizing agent, degradation can be accelerated by heat application during UV irradiation.

Removal of the low-molecular weight components resulting from polymer degradation is preferably carried out in the following manner. The sample comprising the fiber and the absorbent polymer is put into a mesh bag and caused to degrade in the bag. After polymer degradation, the bag and the contents are washed with water, etc. to remove the resulting water-dispersible or water-soluble low-molecular weight components through the mesh of the bag.

The mesh bag to be used can be made of various materials, such as a porous synthetic resin sheet. Materials resistant against the polymer degradation treatment are preferred. The shape of the bag is not limited as long as the sample can be put in. The mesh size of choice is preferably such that does not allow the cellulosic fibers to pass through but allows the low-molecular weight components resulting from polymer degradation to pass through easily. Where the absorbent polymer is degraded to gain water-solubility, the resulting water-soluble low-molecular weight components are allowed to pass through even very small openings that do not let the cellulosic fibers pass. A filter made of a porous material, such as a glass fiber, will do in place of the mesh bag.

After removing the degraded absorbent polymer (preferably the whole amount of the polymer) from the sample, the residue is weighed. The fiber content and/or the absorbent polymer content in the sample can be calculated from the residue weight. For example, the residue weight is taken as the content of the fiber that has been present in the sample under analysis. The difference obtained by subtracting the residue weight from the weight of the sample before polymer degradation is taken as the content of the absorbent polymer that has been present in the sample under analysis. For the purpose of improving measuring accuracy, each of the residue and the sample before polymer degradation is preferably weighed after it is dried at 90 to 105° C. for at least 8 hours and then equilibrated at room temperature (about 25 to 40° C.).

The present invention will now be illustrated in greater detail with reference to Examples, but it should be understood that the invention is not construed as being limited thereto.

(I) Examples of First Aspect of the Invention

EXAMPLE 1

(1) Preparation of Absorbent Member

Absorbent members having the structure shown in FIGS. 2(a) and 2(b) were produced from a superabsorbent polymer and pulp fiber using an apparatus having the configuration shown in FIG. 3.

The shape of forming recesses and arrangement of first and second suction regions in each recess were as shown in FIG. 4(a). The open area ratio of the first suction region 51 and that of the second suction region 52 were 56% and 5%, respectively. The diameters of suction holes provided in both the first and second suction regions all fell within a range of 0.1 to 0.3 mm and averaged 0.2 mm in both regions. Each chamber provided behind the regions 54 to 56 of the drum 5 was maintained at a vacuum pressure lower than atmospheric pressure by 8 to 11 kPa, and this vacuum pressure was exerted to the first and second suction regions 51 and 52.

The area, etc. of the first and second suction regions are shown in Table 1, in which "front" and "rear" correspond to the first suction region and the second suction region, respectively. The amounts of the pulp fiber and the superabsorbent polymer that make up one absorbent member were 14 g and 12 g, respectively. A polyacrylic acid-based superabsorbent polymer was used.

EXAMPLES 2 AND 3

Absorbent members were produced in the same manner as in Example 1, except for changing the open area ratio of the second suction region 52 to 10% (Example 2) or 18% (Example 3).

Comparative Example 1

Absorbent members were produced in the same manner as in Example 1, except for changing the open area ratio of the first suction region 51 to 50% and that of the second suction region 52 to 25%. The amount of the superabsorbent polymer that make up one absorbent member was 14 g.

Comparative Example 2

Absorbent members were produced in the same manner as in Example 1, except that each recess had an open area ratio of 40% all over its bottom.

EXAMPLE 4

Figure 5:
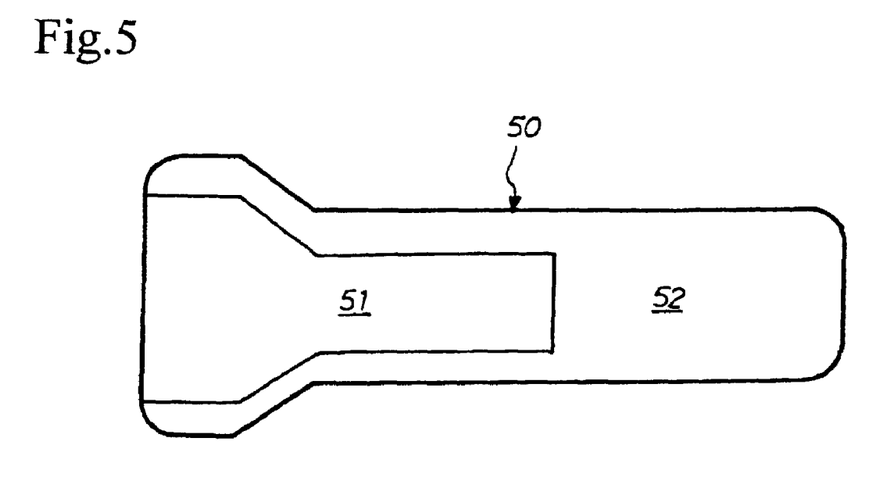
FIG. 5 depicts another example of the configuration of the first and the second suction regions.

Absorbent members were produced in the same manner as in Example 1, except for changing the arrangement of the first and second suction regions as illustrated in FIG. 5. In Table 1, "T" and "Y" correspond to the first and the second suction regions, respectively.

(2) Absorbent Member

The absorbent members obtained in Examples 1 to 4 and Comparative Examples 1 and 2 were measured for the pulp and the polymer contents in each of the portion corresponding to the first suction region (i.e., the high basis weight portion 41, represented by "front" or "T" in Table 1) and the portion corresponding to the second suction region (i.e., the low basis weight portion 42, represented by "rear" or "Y" in Table 1). The weights and specific contents (contents per unit area) of the pulp fiber and the polymer in each portion, and the like are shown in Table 1.

(3) Evaluation of Absorbent Member

Disposable pull-on diapers were produced using the absorbent members prepared in the Examples and Comparative Examples. The design and materials of the disposable diapers were the same as those of a commercially available disposable pull-on diaper (Merries Pants Morenai-Smart, available from Kao Corp.), except that the absorbent members prepared in the Examples and Comparative Examples were used. Each absorbent member was arranged such that the high basis weight portion was located on the stomach side of the disposable diaper.

The resulting diapers were evaluated for leakproofness in accordance with the following leak test method. The results obtained are shown in Table 1.

Leak Test:

A pull-on diaper was put on a human body model having an outlet for urination on the front side of the model. The model with the diaper on was laid on its stomach, and physiological saline was poured from the outlet into the diaper at a rate of 10 g/sec. Each time 50 g of saline was poured, pouring was stopped for 10 seconds and then resumed. The total weight of saline poured until it began to leak from the front waist end was taken as a measure for front leakproofness.

in the form of a dispersion in an air stream directed to the outer periphery of a forming drum, depositing the superabsorbent polymer and the pulp fiber in a recess by suction through a large number of suction holes of the bottom of the recess, and releasing the air-laid aggregate from the recess.

The bottom of the recess is formed of a foraminous plate having no level difference. The plate had an open area ratio of 60% in its forward region and of 15% in its rearward region. The chamber in the forming drum was evacuated to a pressure lower than atmospheric pressure by 8 to 11 kPa (measured values with pressure fluctuation taken into account) so that the negative pressure might be applied to the foraminous bottom of the recess. The superabsorbent polymer and the pulp fiber were fed at a weight ratio of 55/45. After air-laying, the resulting air-laid aggregate was not pressed. A polyacrylic acid-based superabsorbent polymer was used.

EXAMPLE 6

An absorbent member was produced in the same manner as in Example 5, except for changing the open area ratios of the forward region and the rearward region to 50% and 3%, respectively.

TABLE 1

|  | Example 1 | | Example 2 | | Example 3 | | Comparative Example 1 | | Comparative Example 2 | | Example 4 | |
| --- | --- | --- | --- | --- | --- | --- | --- | --- | --- | --- | --- | --- |
|  | front | rear | front | rear | front | rear | front | rear | front | rear | T | Y |
| Recess: | | | | | | | | | | | | |
| Open area ratio (%) (R1\|R2) | 56 | 5 | 56 | 10 | 56 | 18 | 50 | 25 | 40 | 40 | 56 | 10 |
| R1:R2 | 92:8 | | 85:15 | | 76:24 | | 67:33 | | 50:50 | | 85:15 | |
| Area ratio | 35:65 | | 35:65 | | 35:65 | | 35:65 | | 35:65 | | 30:70 | |
| Absorbent Member: | | | | | | | | | | | | |
| Pulp specific content ratio | 70:30 | | 64:36 | | 57:43 | | 53:47 | | 49:51 | | 66:34 | |
| Pulp weight ratio | 84:16 | | 80:20 | | 75:25 | | | | | | 58:42 | |
| Polymer specific content ratio | 69:31 | | 60:40 | | 53:48 | | 50:50 | | 50:50 | | 60:40 | |
| Polymer weight ratio | 84:16 | | 77:23 | | 72:28 | | | | | | 53:47 | |
| Total pulp weight (g/member) | 14 | | 14 | | 14 | | 14 | | 14 | | 14 | |
| Total polymer weight (g/member) | 12 | | 12 | | 12 | | 14 | | 12 | | 12 | |
| Pulp/polymer mixing weight ratio | 54/46 | 57/43 | 56/44 | 54/46 | 56/44 | 53/47 | 49/51 | 57/43 | 55/45 | 54/46 | 55/46 | 55/45 |
| Front leakproofness (g) | 326 | | 281 | | 280 | | 230 | | 230 | | 280 | |

It is seen from the results in Table 1 that a portion with increased absorption capacity over the other portion is sufficiently formed in the absorbent members of the Examples and that the absorbing performance of that portion is sufficiently manifested. In contrast, the absorbent members of Comparative Examples fail to have a high basis weight in their front portion (Comparative Example 1) or show a large difference in pulp/polymer mixing weight ratio between the front and rear portions, resulting in a failure to exhibit expected front leakproofness.

It is also seen that use of the absorbent members of Examples brings about improvement on leakproof performance of disposable diapers while minimizing the total amount of the superabsorbent polymer to be used.

(II) Examples of Second and Third Aspects of the Invention

EXAMPLE 5

An absorbent member was produced by a method which comprises feeding a superabsorbent polymer and pulp fiber

EXAMPLE 7

An absorbent member was produced in the same manner as in Example 5, except for changing the open area ratios of the forward region and the rearward region to 50% and 7%, respectively.

EXAMPLE 8

An absorbent member was produced in the same manner as in Example 5, except that the chamber was evacuated to a pressure lower than atmospheric pressure by 6to 9kPa.

Comparative Example 3

An absorbent member was produced in the same manner as in Example 5, except for changing the open area ratios of the forward region and the rearward region to 60% and 30%, respectively.

The absorbent members prepared in Examples 5 to 8 and Comparative Example 3 were each measured for polymer/pulp fiber mixing ratio and thickness in each of the high basis weight portion and the low basis weight portion. The results obtained are shown in Table 2 below. As for the absorbent member of Comparative Example 3, the portion formed on the region with a higher open area ratio and the portion formed on the region with a lower open area ratio were regarded as the high basis weight portion and the low basis weight portion for the sake of convenience.

Evaluation of Absorbent Member:

(1) Leak Test

The absorbent member (80 mm wide and 200 mm long) was fixed on a smooth surface inclined at 45°, and artificial urine was poured thereon at a rate of 5 ml/sec at a point 140 mm up from the lower end of the absorbent member (the pouring point was in the high basis weight portion). Every time 40 ml of artificial urine was poured, pouring was stopped for 5 minutes and then resumed. The total amount of the artificial urine poured until the absorbent member began to leak from its lower end was taken as a measure for front leakproofness of the absorbent member. The results obtained are shown in Table 2.

(2) Texture

When stroked with the hand in the longitudinal direction, the absorbent members of Examples 5 to 8 gave no distinct and uncomfortable feeling of level difference. In particular the absorbent members of Examples 5 and 8, having a thickness difference as small as about 0.5 mm, felt as if there was no level difference.

mentioned effects are not expected of this comparative absorbent member.

(III) Examples of Fourth Aspect of the Invention

EXAMPLE 9

(1) Preparation of Sample

Samples described below were prepared using pulp fiber (NB416, available from Weyerhaeuser) and an absorbent polymer mainly comprising sodium polyacrylate (BC283FA, available from Taiwan Plastic).

Samples prepared using 6 g, 10 g, and 18 g of the pulp fiber, prepared in triplicate (designated samples P1 through P9).

Samples prepared using 5 g, 10 g, and 15 g of the absorbent polymer, prepared in triplicate (designated samples S1 through S9).

Samples prepared using the pulp fiber and the absorbent polymer in pulp/polymer amounts of 6 g/5 g, 10 g/10 g, and 18 g/15 g, prepared in triplicate (designated samples PS1 through PS9).

The pulp fiber and the absorbent polymer were each dried at 90° C. for 18 hours or longer, equilibrated at room temperature (around 25° C.), and weighed. The accurate weight of the pulp fiber and/or the absorbent polymer in these samples will hereinafter be referred to as "the known weight".

(2) Polymer Degradation

Each sample was put into a mesh bag whose weight had been precisely weighed. Each bag containing the sample was immersed in an aqueous solution containing 4 wt % ascorbic acid and 0.02 wt % riboflavin to sufficiently

TABLE 2

|  |  | Example | | | | Comparative |
|---|---|---|---|---|---|---|
|  |  | 5 | 6 | 7 | 8 | Example 3 |
| Basis | High basis weight portion | 270 | 325 | 300 | 270 | 250 |
| Weight (g/m$^2$) | Low basis weight portion | 240 | 140 | 200 | 240 | 250 |
| Polymer/pulp | High basis weight portion | 54/46 | 54/46 | 57/43 | 56/44 | 52/48 |
| Mixing Weight Ratio | Low basis weight portion | 55/45 | 57/43 | 52/48 | 52/48 | 59/41 |
| Thick-ness (mm) | High basis weight portion | 5 | 7 | 6 | 5 | 5 |
|  | Low basis weight portion | 4.5 | 3 | 4 | 4.5 | 5 |
| Front Leakproofness (ml) |  | 280 | 320 | 280 | 280 | 230 |

All the absorbent members prepared in Examples 5 to 8 had a high basis weight portion in the forward portion thereof with a larger thickness than that of the rearward portion. The two portions showed not so large a difference in polymer/pulp fiber mixing ratio and were equal in density. Therefore, these absorbent members suffer from no gel blocking in their high basis weight portion contemplated to exhibit increased absorption capacity and are designed to have the high basis weight portion efficiently manifest its absorbing performance to the fullest. Besides, unlike conventional two-plied absorbent members, the absorbent members of the Examples hardly show a large difference in stiffness between the high and low basis weight portions. On the other hand, the absorbent member of Comparative Example 3 developed no difference in thickness and no desirable difference in basis weight. As a result, the aboveimpregnate the sample with the solution. The mesh bag was taken out of the solution and exposed to sunlight for 8 hours per day for three consecutive days to degrade the polymer into solubilized low-molecular weight components. The mesh bag was washed with water to remove the low-molecular weight components. Where the color of the riboflavin-stained polymer did not disappear or where a slimy feel in washing did not disappear, the mesh bag was repeatedly subjected to immersion in the same aqueous solution as used above followed by exposure to sunlight in the same manner as described above until the color of the riboflavin-stained polymer and the slimy feel in washing disappeared.

(3) Weighing

After thorough washing, the mesh bag was dewatered by centrifugation at 800 rpm for 10 minutes, dried at 90° C. for 18 hours or longer, equilibrated at room temperature (25°

C.), and weighed to obtain the weight of the mesh bag containing the residue (hereinafter also referred to as "the post-treatment weight").

(4) Determination of Fiber and Absorbent Polymer by Calculation

Figure 7:
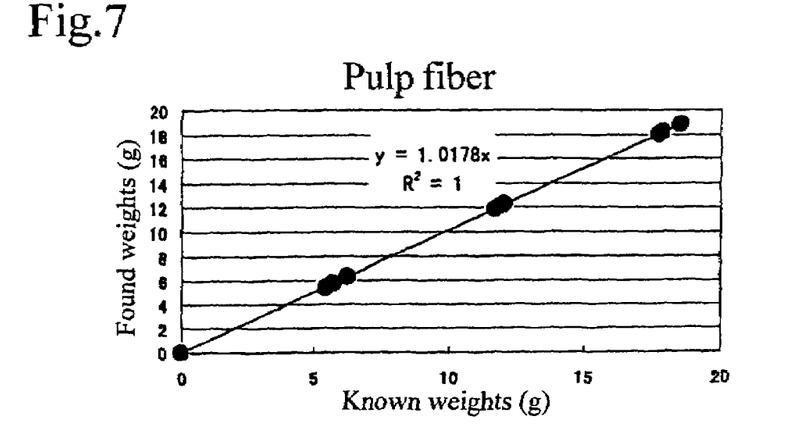
FIG. 7 is a graph showing the correlation between measured pulp fiber contents and amounts of pulp fiber used in samples made solely of pulp fiber.

As for samples P1 to P9, the difference calculated by subtracting the weight of the mesh bag from the post-treatment weight was taken as the found weight of the pulp fiber. Table 3 shows the weight of the mesh bag only (bag weight), the known weight of pulp fiber, the post-treatment weight, the found weight, and the error of determination (represented in terms of percentage of the found weight to the known weight). FIG. 7 graphically represents the correlation between the found weights and the known weights of the pulp fiber. In FIG. 7 are also shown the results of regression analysis (slope constant and correlation coefficient).

Figure 8:
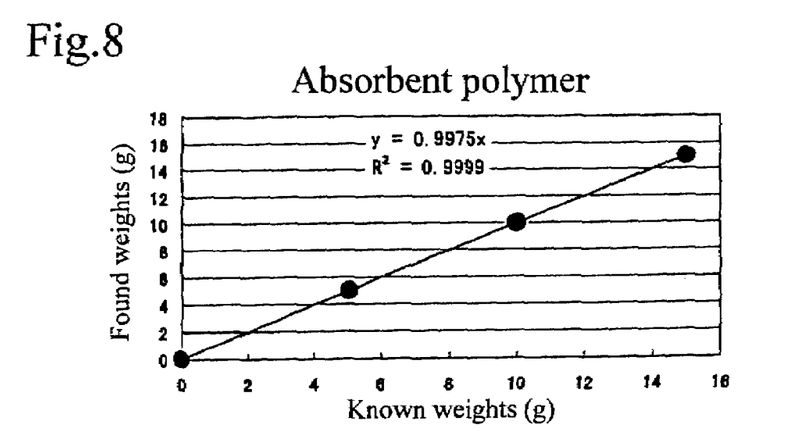
FIG. 8 is a graph showing the correlation between measured absorbent polymer contents and amounts of absorbent polymer used in samples made solely of absorbent polymer.

As for samples S1 to S9, the difference obtained by subtracting the post-treatment weight from the total of the known polymer weight and the mesh bag weight was takenas the found weight of the polymer. Table 4 shows the mesh bag weight, the known polymer weight, the post-treatment weight, the found polymer weight, and the error of determination (represented in terms of percentage of the found weight to the known weight). FIG. 8 graphically represents the correlation between the found weights and the known weights of the absorbent polymer. In FIG. 8 are also shown the results of regression analysis (slope constant and correlation coefficient).

Figure 9:
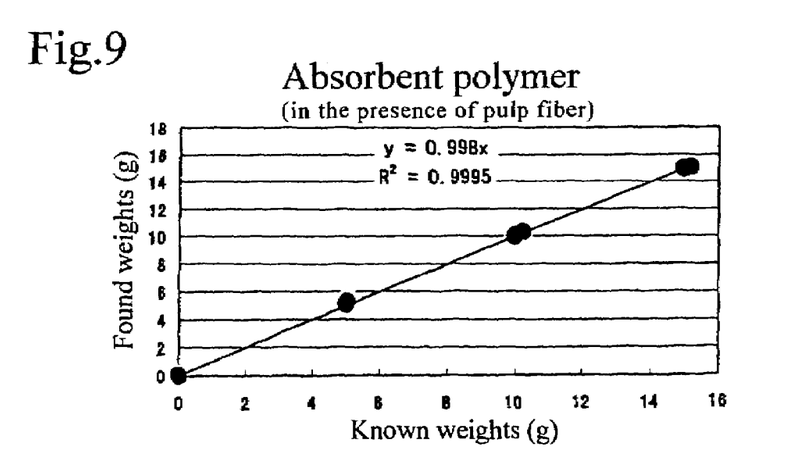
FIG. 9 is a graph showing the correlation between measured absorbent polymer contents and amounts of absorbent polymer used in samples made of absorbent polymer and pulp fiber.

As for samples PS1 to PS9, the difference obtained by subtracting the mesh bag weight from the post-treatment weight was taken as the found weight of the pulp fiber, and the difference calculated by subtracting the post-treatment weight from the total of the known pulp weight and the known polymer weight was taken as the found weight of the absorbent polymer. Table 5 shows the mesh bag weight, the known weights of the pulp fiber and the absorbent polymer, the post-treatment weight, the found weights of the pulp and the polymer, and the error of determination (represented in terms of percentage of the found weight to the known weight). FIG. 9 graphically represents the correlation between the known weights of the absorbent polymer and the weights of the absorbent polymer as measured in the presence of pulp fiber. In FIG. 9 are also shown the results of regression analysis (slope constant and correlation coefficient).

TABLE 3

| Sample | Bag Weight (g) | Known Pulp Fiber Weight (g) | Post-Treatment Weight (g) | Found Pulp Fiber Weight (g) | Error (%) |
|---|---|---|---|---|---|
| P1 | 5.11 | 5.44 | 10.58 | 5.47 | 100.6 |
| P2 | 5.13 | 6.21 | 11.46 | 6.33 | 101.9 |
| P3 | 5.10 | 5.71 | 10.90 | 5.80 | 101.6 |
| P4 | 5.08 | 11.84 | 17.15 | 12.07 | 101.9 |
| P5 | 5.15 | 11.72 | 17.05 | 11.90 | 101.5 |
| P6 | 5.15 | 12.08 | 17.51 | 12.36 | 102.3 |
| P7 | 4.53 | 18.52 | 23.36 | 18.83 | 101.7 |
| P8 | 4.49 | 17.87 | 22.72 | 18.23 | 102.0 |
| P9 | 4.51 | 17.76 | 22.55 | 18.04 | 101.6 |
| | | | | Average error | 101.68 |

TABLE 4

| Sample | Bag Weight (g) | Known Pulp Fiber Weight (g) | Post-Treatment Weight (g) | Found Pulp Fiber Weight(g) | Error (%) |
|---|---|---|---|---|---|
| S1 | 5.17 | 5.01 | 5.19 | 4.99 | 99.6 |
| S2 | 5.17 | 5.00 | 5.16 | 5.01 | 100.2 |
| S3 | 5.26 | 5.03 | 5.21 | 5.08 | 101.0 |
| S4 | 5.24 | 9.99 | 5.24 | 9.99 | 100.0 |
| S5 | 5.28 | 10.07 | 5.26 | 10.09 | 100.2 |
| S6 | 5.22 | 10.04 | 5.33 | 9.93 | 98.9 |
| S7 | 5.30 | 15.04 | 5.41 | 14.93 | 99.3 |
| S8 | 5.31 | 15.00 | 5.34 | 14.97 | 99.8 |
| S9 | 5.33 | 14.98 | 5.32 | 14.99 | 100.1 |
| | | | | Average error | 99.89 |

TABLE 5

| | | Known | | | Found | | Error | |
|---|---|---|---|---|---|---|---|---|
| Sample | Bag Weight (g) | Known Fiber Weight (g) | Polymer Weight (g) | Post-Treatment Weight (g) | Found Fiber Weight (g) | Polymer Weight (g) | Fiber Weight (%) | Polymer Weight (%) |
| PS1 | 5.27 | 6.10 | 5.00 | 11.29 | 6.02 | 5.08 | 98.7 | 101.6 |
| PS2 | 5.29 | 5.83 | 5.06 | 10.91 | 5.62 | 5.27 | 96.4 | 104.2 |
| PS3 | 5.20 | 6.14 | 5.02 | 11.18 | 5.98 | 5.18 | 97.4 | 103.2 |
| PS4 | 4.78 | 10.39 | 10.26 | 15.11 | 10.33 | 10.32 | 99.4 | 100.6 |
| PS5 | 4.46 | 12.42 | 10.05 | 16.84 | 12.38 | 10.09 | 99.7 | 100.4 |
| PS5 | 4.49 | 11.70 | 10.00 | 16.26 | 11.77 | 9.93 | 100.6 | 99.3 |
| PS7 | 4.45 | 18.31 | 15.20 | 22.89 | 18.44 | 15.07 | 100.7 | 99.1 |
| PS8 | 4.53 | 17.74 | 15.01 | 22.39 | 17.86 | 14.89 | 100.7 | 99.2 |
| PS9 | 4.54 | 18.40 | 14.99 | 23.00 | 18.46 | 14.93 | 100.3 | 99.6 |
| | | | | | | Average Error | 99.32 | 100.80 |

Tables 3 to 5 and FIGS. 7 to 9 reveal the following. The slope constant and the correlation coefficient are both approximately 1.0 irrespective of the sample composition (pulp fiber alone, absorbent polymer alone, or pulp fiber/polymer mixture). With respect to samples PS1 to PS9 (Table 5), the average error of the found values of pulp fiber weight is 99.32% (deviation: 0.68%), that of absorbent polymer weight is 100.8% (deviation: 0.8%), and the greatest of the errors is 104.2% (deviation: 4.2%) as for the polymer weight. It is understood from these results that the determining?? method of the present invention makes it feasible to quantitatively determine the pulp fiber and the absorbent polymer accurately and easily.

EXAMPLE 10

Samples consisting solely of an absorbent polymer and samples consisting of pulp fiber and an absorbent polymer were prepared in the same manner as in Example 9, except for using the following four kinds of polyacrylic acid-based polymers as an absorbent polymer.

Polymer 1: EQ-R, available from Kao Corp.
Polymer 2: CAW4, from Nippon Shokubai Co., Ltd.
Polymer 3: CAW16, from Nippon Shokubai Co., Ltd.
Polymer 4: IM5800, from Sanyo Chemical Industries, Ltd.

The weight of the polymer of each sample was determined in the same manner as in Example 9, and the found values were analyzed by regression. The results obtained (slope constant and correlation coefficient) are shown in Table 6 below.

TABLE 6

| | | Slope Constant | Correlation Coefficient |
|---|---|---|---|
| Polymer 1 | polymer alone | 1.00 | 1.000 |
| | with pulp fiber | 1.02 | 0.999 |
| Polymer 2 | polymer alone | 0.98 | 1.000 |
| | with pulp fiber | 1.01 | 0.998 |
| Polymer 3 | polymer alone | 0.99 | 1.000 |
| | with pulp fiber | 1.03 | 0.998 |
| Polymer 4 | polymer alone | 0.98 | 0.997 |
| | with pulp fiber | 1.02 | 0.998 |

It is seen from Table 6 that the slope constant and the correlation coefficient are both approximate to 1.0 irrespective of the kind (characteristics) of the absorbent polymer. This means there is no necessity to prepare a calibration curve for every polymer kind. All the absolute errors were found to be less than 1%, proving the high accuracy of the determination.

The determining method of the present invention is particularly suited to quantitatively determine each component of a sample containing a cellulosic fiber and a polyacrylic acid-based absorbent polymer. Where a sample contains a water-soluble third component, the third component is first washed away from the sample with water, etc., and the remaining mixture of the fiber and the polymer is subjected to quantitative analysis by the determining method of the invention.

The method of producing an absorbent member according to the present invention efficiently and economically provides an absorbent member having excellent absorbing performance which is designed to have an increased absorption capacity in one part and to allow that part to fully exhibit its absorbency.

The absorbent member according to the present invention is designed to have an increased absorption capacity in one part and to allow that part to fully exhibit its absorbency and, when used in an absorbent article, gives little uncomfortable feeling to a wearer.

The absorbent article according to the present invention exhibits excellent absorbing performance and feels comfortable, enjoying the full effects of the absorbent member of the invention.

The method of determining fiber and/or an absorbent polymer according to the present invention enables accurate quantitative determination of a cellulosic fiber and/or a polyacrylic acid-based absorbent polymer in a mixture comprising the same.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application Nos. 2002-168650 filed Jun. 10, 2002, 2002-168651 filed Jun. 10, 2002, 2003-112200 filed Apr. 16, 2003, 2003-121073 filed Apr. 25, 2003, and 2003-121074 filed Apr. 25, 2003, which are incorporated herein by reference.

What is claimed is:

1. A method of producing an absorbent member comprising feeding a superabsorbent polymer and pulp fiber both in the form of a dispersion in an air stream, depositing the superabsorbent polymer and the pulp fiber in a flat bottom recess by suction through a plurality of suction holes provided in the bottom of the recess, and releasing the deposited aggregate from the recess, wherein the flat bottom of the recess has a first suction region (51) having an open area ratio R1 of 40 to 80% and a second suction region (52) having an open area ratio R2 of 2 to 20% with the ratio of R1 to R2 ranging from 70/30 to 99/1, the superabsorbent polymer and the pulp fiber are deposited on both the first and the second suction regions, wherein a difference in open area ratio R between the first and the second suction regions (51) and (52) is made by forming suction holes at pitches different between the two regions and wherein the suction holes have an average diameter of 0.05 to 0.5 mm in each of the first and second suction regions.

2. The method of producing an absorbent member according to claim 1, wherein the flat bottom of the recess is substantially free from a level difference between the first suction region and the second suction region as means for controlling the thickness of the deposition of the superabsorbent polymer and the pulp fiber.

3. The method of producing an absorbent member according to claim 1, wherein the deposition of the superabsorbent polymer and the pulp fiber in the flat bottom recess is carried out by applying vacuum pressure lower than atmospheric pressure by 1 to 20 kPa to the first and the second suction regions from behind the bottom of the recess.

4. The method of producing an absorbent member according to claim 2, wherein the superabsorbent polymer and the pulp fiber are dispersed in an air stream in the form of a mixture thereof.

5. The method of producing an absorbent member according to claim 1, wherein the diameters of suction holes provided in the first and second suction regions fall within a range of 0.1 to 0.3 mm and average 0.2 mm in each of the first and second suctions regions.

6. The method of producing an absorbent member according to claim 1, wherein the difference in open area ratio R between the first and the second suction regions (51) and (52) is made by forming suction holes of the same size at pitches different between the two regions.

7. The method of producing an absorbent member according to claim 5, wherein the difference in open area ratio R between the first and the second suction regions (51) and (52) is made by forming suction holes of the same size at pitches different between the two regions.

8. The method of producing an absorbent member according to claim 1, wherein substantially all of the suction holes in the first and second suction regions have a diameter falling within the range of 0.05 to 0.5 mm.

* * * * *